United States Patent [19]

Endo

[11] Patent Number: 5,801,049
[45] Date of Patent: Sep. 1, 1998

[54] FREEZE-RESISTANT BAKER'S YEAST STRAIN HAVING SUGAR RESISTANCE

[75] Inventor: Hisanori Endo, Mishima, Japan

[73] Assignee: Asahi Kasei Kogyo Kabushiki Kaisha, Osaka, Japan

[21] Appl. No.: 500,459

[22] Filed: Jul. 10, 1995

[51] Int. Cl.$^6$ ............................................. C12N 1/18
[52] U.S. Cl. ............................ 435/255.2; 435/172.1; 426/19; 426/62
[58] Field of Search ...................... 435/255.2, 172.1; 426/19, 62

[56] References Cited

U.S. PATENT DOCUMENTS 4,547,374 10/1985 Nakatomi et al. .
5,352,606 10/1994 Takano et al. .

FOREIGN PATENT DOCUMENTS

| 0196233 | 8/1990 | European Pat. Off. . |
| 59-25584 | 6/1984 | Japan . |
| 59-203442 | 11/1984 | Japan . |
| 59-48607 | 11/1984 | Japan . |
| 61-254186 | 11/1986 | Japan . |
| 62-208273 | 9/1987 | Japan . |
| 1-16155 | 3/1989 | Japan . |
| 4-20595 | 4/1992 | Japan . |

OTHER PUBLICATIONS

Yasunaga et al, The Food Industry, vol. 37, No. 24, pp. 68–73 (Dec. 30, 1994) (Partial Translation).
Itoi et al, Technology for changing and improving functions of foods, pp. 249–273 (Nov. 1, 1994) (Partial Translation).

*Primary Examiner*—Irene Marx
*Attorney, Agent, or Firm*—Birch, Stewart, Kolasch & Birch, LLP

[57] ABSTRACT

Disclosed is a yeast strain belonging to *Saccharomyces cerevisiae*, having a freeze resistance and having an invertase activity of not less than a value corresponding to a minimum level of sucrose decomposing ability effective for utilizing sucrose for fermentation, but of not more than 200 U/g, in terms of the value of activity as measured with respect to the yeast in a state of non-freeze compressed yeast having a water content of 67% by weight and a solids content of 33% by weight. The baker's yeast of the present invention has not only freeze resistance but also high resistance to a super high sugar content dough.

1 Claim, No Drawings

FREEZE-RESISTANT BAKER'S YEAST STRAIN HAVING SUGAR RESISTANCE

BACKGROUND OF THE INVENTION

1. Field Of The Invention

The present invention relates to a novel freeze-resistant baker's yeast having sugar resistance. More particularly, the present invention is concerned with a baker's yeast belonging to *Saccharomyces cerevisiae*, wich has not only freeze resistance but also a specific, relatively low non-freeze invertase activity which leads to a high fermentative ability on a super high sugar content dough.

The baker's yeast of the present invention has not only freeze resistance but also high resistance to a super high sugar content dough. By virtue of such excellent properties of the yeast of the present invention, with respect to a moderate to high sugar content dough, especially a high to super high sugar content dough, not only can a shortening of a proofing time be achieved, but also a high quality bread having excellent properties, such as large volume, excellent light brown color, lustrous and less mottled surface, and the like, can be produced. Further, a dough prepared by using the yeast of the present invention is resistant to weakening in mass cohesion during freezing preservation, so that it can maintain an appropriate firmness and prevent the shape thereof from changing under its own weight even after thawing, thereby ensuring the production of a bread having a good shape.

2. Prior Art

Frozen dough for bread has great advantages in that it is useful in providing fresh-baked bread, and can improve productivity and facilitate personnel management due to, e.g. its capability of simplifying the bread production process (saving on the manpower), eliminating nighttime and early morning operations, and the like. Therefore, techniques of producing bread from frozen dough are attracting attention in the baking industry. Frozen dough is produced by a method in which a kneaded mixture of bread ingredients, e.g. flour, sugar, salt, fat, dairy products, water, and the like, is subjected to fermentation, the resultant fermented dough is divided into portions, and each portion is frozen and preserved at about −20° C. The frozen portion of dough is thawed, molded, subjected to proofing, and baked. The molding may be conducted before the freezing.

It is known that when bread dough prepared by using an ordinary baker's yeast having no freeze resistance is frozen, the baker's yeast suffers a freezing damage, resulting in a lowering of the fermentative ability. As a result, the time required for the proofing (to be conducted after thawing the frozen dough) is prolonged and a reduction in the resultant bread volume occurs.

Therefore, for producing a frozen dough, a baker's yeast which will not be damaged by freeze preservation, i.e. a baker's yeast having excellent freeze resistance, has been developed. For example, the following freeze resistant strains of baker's yeast are conventionally known: *Saccharomyces rosei* (see Examined Japanese Patent Application Publication No. 59-25584), *Saccharomyces cerevisiae* FTY (FRI-413) (see Examined Japanese Patent Application Publication no. 59-48607), *Saccharomyces cerevisiae* IAM 4274 (see Unexamined Japanese Patent Application Laid-Open Specification No. 59-203442), *Saccharomyces cerevisiae* KYF 110 (see Unexamined Japanese Patent Application Laid-Open Specification No. 62-208273, corresponding to EP Publication No. 196233), Saccharomyces species (see Examined Japanese Patent Application Publication No. 1-16155, corresponding to U.S. Pat. No. 4,547,374), and *Saccharomyces cerevisiae* FTY-3 (see Examined Japanese Patent Application Publication No. 4-20595, corresponding to U.S. Pat. No. 5,352,606).

Especially in Japan, sweet bread prepared from dough containing a very large amount of sugar is popular. However, it is known that when a conventional baker's yeast is used in dough containing a large amount of sugar, the yeast suffers a lowering of fermentative ability, so that not only does the dough require a prolonged proofing time, but also the volume of the final bread is caused to be small, irrespective of whether or not the baker's yeast has freeze resistance.

As mentioned above, the conventional freeze resistant baker's yeast is very poor in sugar resistance, so that it could at best only be used in dough having a moderate sugar content (usually less than 20% by weight, based on the weight of a flour in the dough), and it has been very difficult to use the conventional freeze resistant baker's yeasts in a high sugar content dough, especially a super high sugar content dough having a sugar content as high as 35% by weight or more, based on the weight of a flour in the dough.

In Unexamined Japanese Patent Application Laid-Open Specification No. 61-254186, *Saccharomyces cerevisiae* FTY-2 is disclosed as a yeast having sugar resistance. However, it has been found that the sugar resistance of this yeast is lower than that of commercially available baker's yeasts having no freeze resistance.

Therefore, it has been desired to develop a novel strain of baker's yeast having not only high freeze resistance, but also high sugar resistance.

SUMMARY OF THE INVENTION

The present inventor has made extensive and intensive studies with a view toward solving the above-mentioned problems of the prior art, and developing a baker's yeast having not only high freeze resistance but also exhibiting high fermentative ability even on a super high sugar content dough. As a result, the present inventor has succeeded in isolating a novel diploid hybrid yeast strain which has not only freeze resistance, but also an extremely high sugar resistance, as compared to the conventional baker's yeasts. More specifically, this novel diploid hybrid strain of baker's yeast can be obtained by conjugation between a haploid yeast strain obtained from germination of spores from a diploid yeast strain belonging to *Saccharomyces cerevisiae* having a high fermentative ability on a super high sugar content dough but having no freeze resistance and a haploid yeast strain obtained from germination of spores from a diploid yeast strain belonging to *Saccharomyces cerevisiae* having a low fermentative ability on a super high sugar content dough but having a high freeze resistance. With respect to the obtained novel diploid hybrid yeast strain, further studies have been made. Thus, it has been unexpectedly found that the novel diploid hybrid yeast strain has an invertase activity of not less than a value corresponding to a minimum level of sucrose decomposing ability effective for utilizing sucrose for fermentation, but of not more than 200 U/g, in terms of the value of activity as measured with respect to the yeast in a state of non-freeze compressed yeast having a water content of 67% by weight and a solids content of 33% by weight. It has also been found that, by the use of a baker's yeast having such a specific, relatively low invertase activity, a high fermentation performance of a frozen, high sugar content dough can be realized for the first time, so that, even with respect to a frozen, high sugar content dough, especially a super high sugar content dough, not only can a shortening of a proofing time be achieved, but also a high quality bread having excellent properties, such as large volume, good shape, excellent light brown color, lustrous and less mottled surface, and the like, can be produced. The present invention has been completed, based on these novel findings.

Accordingly, it is a primary object of the present invention to provide a yeast strain having not only freeze resistance, but also a high sugar resistance, so that it exhibits high fermentative ability in a moderate to super high sugar content dough, especially in a high to super high sugar content dough.

It is another object of the present invention to provided a yeast strain which is capable of shortening a time required for a proofing process to be performed after thawing of the frozen dough, but also providing a high quality bread having excellent properties, such as large volume, good shape, excellent light brown color, lustrous and less mottled surface, and the like.

The foregoing and other objects, features and advantages of the present invention will be apparent from the following detailed description and claims.

DETAILED DESCRIPTION OF THE INVENTION

According to the present invention, there is provided a yeast strain belonging to *Saccharomyces cerevisiae*, having a freeze resistance; and having an invertase activity of not less than a value corresponding to a minimum level of sucrose decomposing ability effective for utilizing sucrose for fermentation, but of not more than 200 U/g, in terms of the value of activity as measured with respect to the yeast in a state of non-freeze compressed yeast having a water content of 67% by weight and a solids content of 33% by weight.

With the yeast strain of the present invention, it has for the first time been realized to achieve a fermentative ability of 45 ml or more, preferably 50 ml or more in terms of the amount of carbon diozide gas generated by non-freeze fermentation at 38° C. for one hour with respect to 30 g of a super high sugar content dough containing 0.935 g of the yeast, wherein the super high sugar content dough is defined as having a sugar content of 35% by weight, based on the weight of a flour in the dough.

Herein, the term "freeze resistance" means a property such that yeast cells suffer no damage or only little damage by preservation under freeze conditions. The test for freeze resistance is conducted by the following method. A fresh dough is prefermented at 30° C. for 60 minutes and subsequently feremented at 38° C. for 60 minutes, and the amount (ml) of carbon dioxide gas produced during 60 minutes of fermentation at 38° c. is measured and taken as the non-freeze fermentative ability. Separately, the same fresh dough as used above is prefermented at 30° C. for 60 minutes, and then frozen at −20° C. for 14 days. After that period of time, the dough is thawed at 38° C. for 20 minutes, and fermented at 38° C. for 60 minutes. The amount (ml) of carbon dioxide gas produced during 60 minutes of fermentation at 38° C. is measured and taken as the post-freeze fermentative ability. This post-freeze fermentative ability is compared with the non-freeze fermentative ability. Freeze resistance is expressed in terms of a post-freeze residual fermentative ability (%), relative to the non-freeze fermentative ability (100%). For example, with respect to representative yeast strains having freeze resistance, a post-freeze residual fermentative ability of 80% or more is exhibited in a moderate sugar content dough (which has a sugar content of 15% by weight, based on the weight of the flour in the dough), and a post-freeze residual fermentative ability of 85% or more is exhibited in a high sugar content dough (which has a sugar content of 25% by weight, based on the weight of the flour in the dough).

As mentioned above, the sugar content of a dough is expressed in % by weight, based on the weight of the flour in the dough.

In the present invention, the term "non-sugar dough" used hereinbelow means a dough containing no added sugar.

Generally in the art, the term "low sugar content dough" means a dough having a sugar content of less than 10% by weight, based on the weight of the flour, the term "moderate sugar content dough" means a dough having a sugar content of 10 to less than 20% by weight, based on the weight of the flour, the term "high sugar content dough" means a dough having a sugar content of 20 to less than 35% by weight, based on the weight of the flour, and the term "super high sugar content dough" means a dough having a sugar content of 35% by weight or more, based on the weight of the flour.

However, hereinbelow, for convenience's sake, the "low sugar content dough" is represented by a dough having a sugar content of 5% by weight; the "moderate sugar content dough" is represented by a dough having a sugar content of 15% by weight; the "high sugar content dough" is represented by a dough having a sugar content of 25% by weight; and the "super high sugar content dough" is represented by a dough having a sugar content of 35% by weight.

Invertase is an enzyme which decomposes sucrose into glucose and fructose. Baker's yeasts secrete this enzyme, and the secreted enzyme serves to decompose sucrose into glucose and fructose. The baker's yeasts absorb these monosaccharides and utilize them as the carbon source for growth and fermentation.

In the field of baker's yeasts, the term "fermentation" means the production of carbon dioxide gas mainly for inflating the dough.

When a baker's yeast has no invertase activity at all, it cannot live and grow in a culturing medium having no utilizable saccharides other than starch and added sugar. Ordinary baker's yeasts have almost no amylase activity, so that they usually cannot use starch as a carbon source necessary for growth.

Ordinarily, a dough contains a minute amount of monosaccharides originating from a flour and the like other than added sugar and starch, but such a minute amount of monosaccharides is not sufficient for yeasts to produce a satisfactory amount of carbon dioxide gas. Therefore, it is desired that a baker's yeast have an invertase activity of not less than a value corresponding to a minimum level of sucrose decomposing ability effective for utilizing sucrose for fermentation, in terms of the value of activity as measured with respect to the yeast in a state of non-freeze compressed yeast having a water content of 67% by weight and a solids content of 33% by weight. The invertase activity is preferably approximately 50 U/g or more. On the other hand, a baker's yeast showing an invertase activity which is excessively high has the problems mentioned below. Therefore, the invertase activity is preferably approximately 200 U/g or less, more preferably 150 U/g or less, most preferably 140 U/g or less.

When the invertase activity is too high, the sucrose added to the dough is decomposed into monosaccharides to an excessive extent, so that the osmotic pressure of the dough becomes extremely high. This causes the growth environment of the yeast cells to be deteriorated, and hence the fermentation is hindered or inhibited. As a result, the desired high sugar resistance aimed at by the present invention cannot be achieved, so that a non-freeze fermentative ability as high as 45 ml or more in termas of the amount of carbon dioxide gas cannot be exhibited.

Also, it has been confirmed that in a high sugar content dough prepared by using conventional baker's yeast having an excessively high invertase activity, the weight ratio of monosaccharides to sucrose is increased due to the excessive decomposition of sucrose into monosaccharides.

By contrast, in a high sugar (sucrose) content dough which has been prepared by using the baker's yeast of the present invention having a specific, relatively low invertase activity (i.e., 50 to 200 U/g), the degree of decomposition of the sucrose is moderate, and the weight ratio of monosaccharides to sucrose is maintained at an appropriate level.

Further, when the color of the bread produced by using the yeast of the present invention having an invertase activity of 50 to 200 U/g, is compared with the color of the bread produced by using a yeast having too high an invertase activity, the former is lighter and more beautiful than the latter. In this connection, it is noted that when breads are produced from doughs having incorporated therein glucose and fructose together instead of sucrose, wherein the yeast of the present invention having an invertase activity of 50 to 200 U/g and the yeast having too high an invertase activity are individually used, all of the breads have dark colors, irrespective of the type of the yeast employed. These results are well in agreement with the conventional knowledge in the art that the use of glucose and fructose, which are reduced sugars, disadvantageously causes the bread to have a dark color, as compared to the use of sucrose.

On the other hand, in general, breads baked from frozen doughs tend to have a darker color, and therefore it has been necessary to control the baking temperature and the baking time very carefully. By contrast, by using the baker's yeast of the present invention which has a specific, relatively low invertase activity, the color of a bread is easily controllable even with a high sugar (sucrose) content dough.

Further, it has been found that, by the use of the yeast of the present invention, not only can a shortening of a proofing time be achieved, but also a high quality bread having excellent properties, such as large volume, excellent light brown color, lustrous and less mottled surface, and the like, can be produced.

Furthermore, it has also been found that a dough prepared by using the yeast of the present invention is resistant to weakening in mass cohesion during freezing preservation, so that it can maintain an appropriate firmness and prevent the shape thereof from changing under its own weight even after thawing, thereby ensuring the production of a bread having a good shape, as compared to breads prepard by using conventional yeasts.

As mentioned above, in the present invention, the invertase activity value is expressed in terms of the value of activity as measured with respect to the yeast in a state of non-freeze compressed yeast having a water content of 67% by weight and a solids content of 33% by weight.

The above-mentioned compressed yeast can be obtained by a method in which yeast cells are cultured in an ordinary medium, and the resultant cultured broth is immediately subjected to centrifugation, washing and dehydration, so that the water content and the solids content are adjusted to 67% by weight and 33% by weight, respectively. However, the water content of actually obtained compressed yeast is frequently, slightly higher than or lower than 67% by weight and, therefore, the invertase activity value needs to be corrected so as to comply with that of compressed yeast having a water content of 67% by weight and a solids content of 33% by weight. The correction can be easily made by the following formula:

$$\text{Invertase activity (with respect to compressed yeast having a solids content of 33\% by weight)} = \text{Invertase activity of actually obtained compressed yeast} \times \frac{33}{\text{Solids content of actually obtained compressed yeast}}$$

As mentioned above, the baker's yeast of the present invention exhibits a non-freeze fermentative ability of 45 ml or more, preferably 50 ml or more in terms of the amount of carbon dioxide gas generated by fermentation at 38° C. for one hour with respect to 30 g of a super high sugar content dough containing 0.935 g of the yeast, wherein the super high sugar content dough, as mentioned above, is defined as having a sugar content of 35% by weight, based on the weight of a flour in the dough. With respect to the non-freeze fermentative ability of the yeast of the present invention on doughs having sugar contents other than mentioned above, the following preferable values can be achieved: 160 ml or more for a low sugar content dough having a sugar content of 5% by weight; 150 ml or more for a moderate sugar content dough having a sugar content of 15% by weight; and 85 ml or more for a high sugar content dough having a sugar content of 25% by weight. In a non-sugar dough having no sugar added, the non-freeze fermentative ability is in the range of from 70 to 90 ml.

In use, the yeast of the present invention is added to dough ingredients and the resultant mixture is kneaded to produce dough having excellent fermentation characteristics. Examples of doughs which can be produced by using the yeast of the present invention include bread dough, "manjyuu" (Japanese bun) dough, pizza dough, and the like.

The respective types of dough ingredients depend on the type of the dough to be produced. For example, in producing a bread dough, the dough ingredients include flour, saccharide, fat, egg, dairy products, water and additives such as yeast food, an emulsifying agent and the like. Sucrose is commonly used as the sugar. Other saccharides, such as glucose, fructose and the like can optionally be used in an amount such as not to spoil the desired properties of the dough.

By mixture the above-mentioned dough ingredients and the baker's yeast of the present invention, using a mixer or the like, a dough can be prepared. The production of a dough containing the yeast of the present invention can be conducted in substantially the same manner and under subatnatially the same conditions (including the amoubnt of the yeast) as in the production of doughs containing a conventional yeast. With respect to the production of doughs, reference can be made to, for example, U.S. Pat. Nos. 4,680,182 and 5,352,606.

In general, a freeze type dough is processed in accordance with the steps of preliminary fermentation, freezing, molding and final fermentation (proofing). The use of the baker's yeast of the present invention is advantageous especially when a fermentation of a frozen dough containing a large amount of sucrose is intended.

As representative methods for producing dough or bread, a straight dough method and a sponge and dough method can be mentioned. The straight dough method is a method in which a dough is prepared, subjected to preliminary fermentation, divided into portions, and subjected to molding and final fermentation. Alternatively, if desired, freezing can be conducted before or after the molding. When the freezing is conducted, the preliminary fermentation may be omitted. The sponge and dough method is a method in which a "sponge" dough is prepared, using a part of each of the dough ingredients including baker's yeast, flour, water and the like, and is subjected to so-called sponge fermentation, to form a fermented sponge dough whereupon the remaining part of each of the dough ingredients are added to the fermented sponge dough to obtain a final dough and subsequently, the final dough is divided into portions and subjected to molding and final fermentation. In the sponge and dough method, freezing can be conducted before or after the molding. The resultant fermented dough, even if obtained by any of the above methods, is ultimately baked to produce bread.

With respect to the details of the production of doughs and breads, a number of long-established literatures have been known in the art, which can be consulted, if desired.

The baker's yeast of the present invention can be obtained by the following method. A haploid yeast strain is obtained from germination of spores from a diploid yeast strain belonging to Saccharomyces cerevisiae having a high fermentative ability on a super high sugar content dough and a low invertase activity but having no freeze resistance. Similarly, a haploid yeast strain is obtained from germination of spores from a diploid yeast strain belonging to Saccharomyces cerevisiae having a low fermentative ability on a super high sugar content dough but having a high freeze resistance. Conjugation is conducted between both of the above-obtained two different haploid yeast strains to thereby obtain hybrid yeast strains. Then, the obtained hybrid yeast strains are subjected to screening by the screening method (which is mentioned below) to select strains having freeze resistance. Further, the thus selected strains are subjected to further screening to select strains having a low invertase activity of, for example, from 50 to 200 U/g. If desired, a test can be conducted for confirming that the selected strains have a non-freeze fermentative ability of 45 ml or more in terms of the amount of carbon dioxide gas generated by fermentation at 38° C. for one hour with respect to 30 g of a super high sugar content dough containing 0.935 g of the yeast and having a sugar content of 35% by weight, based on the weight of a flour in the dough.

Microorganisms can be mutated spontaneously or artificially. Hence, any yeast strains satisfying the aforementioned requirements defined in the present invention, i.e., yeast strains having a freeze resistance and having the specific, relatively low invertase activity defined in the present invention, should be construed as falling within the scope of the present invention.

Preferred examples of yeast strains falling in the definition of the yeast of the present invention include Saccharomyces cerevisiae F-26 of the present invention which is illustrated below.

Saccharomyces cerevisiae F-26 has been deposited with the National Institute of Bioscience and Human-Technology, Agency of Industrial Science and Technology, (having a principal office at 1-3, Higashi 1-chome, Tsukuba-shi, Ibaraki-ken, Japan) under the deposition number of FERM BP-5150 on 27 Jun., 1995.

The mycological properties of Saccharomyces cerevisiae F-26 are as follows:

a. Morphology: circular or elliptic
b. Size: 2 to 10 μm×4 to 15 μm
c. Sporulation: positive
d. Utilization of carbon source:

|  | Assimilation | Fermentation ($CO_2$ production) |
|---|---|---|
| D-glucose | + | + |
| D-galactose | + | + |
| Maltose | + | + |
| Sucrose | + | + |
| Lactose | − | − |
| Galactose | + | + |
| Raffinose | + | ± |
| Starch | − | − | e. Nitrate assimilation: negative
f. Vitamine requirements:

| Biotin | + |
|---|---|
| Folic acid | − |
| Nicotinic acid | − |
| Thiamine | − |
| Riboflavin | − |
| Calcium pantothenate | + |
| Inositol | − |
| Pyridoxine | − |
| p-Aminobenzoic acid | − |

With respect to the sporulation, i.e., item c mentioned above, the test for sporulative ability was conducted by the following method. First, yeast cells were inoculated on a YPD agar medium having the following composition, and a preculturing was done for 24 hours at 30° C.

| Composition of YPD agar medium (pH 5.5) | |
|---|---|
| yeast extract (Lot. 012701, manufactured by Difco Laboratories, U.S.A.) | 5 g |
| peptone (Lot. 018802, manufactured by Difco Laboratories, U.S.A.) | 10 g |
| glucose | 40 g |
| $KH_2PO_4$ | 5 g |
| $MgSO_4 \cdot 7H_2O$ | 2 g |
| agar | 20 g |
| distilled water | 1000 ml |

Then, the yeast cells were inoculated on a Sherman's agar medium having the following composition, and cultured for 3 to 10 days at 25° C. to examine whether or not sporulation had occurred.

| Composition of Sherman's agar medium (pH 7.2) | |
|---|---|
| potassium acetate | 1.0 g |
| yeast extract (Lot. 012701, manufactured by Difco Laboratories, U.S.A.) | 0.1 g |
| glucose | 0.05 g |
| agar | 2.0 g |
| distilled water | 100 ml |

Further, it was found that Saccharomyces cerevisiae F-26 was a diploid strain.

*Saccharomyces cerevisiae* F-26 was formerly designated as *Saccharomyces cerevisiae* 3-2-C-7, and deposited with the National Institute of Bioscience and Human-Technology, Japan at the domestic depositary under the accession number FERM P-14013 on Dec. 10, 1993.

To produce the baker's yeast strain of the present invention, breeding techniques other than the above-mentioned conjugation method, e.g., cell fusion method, mutation method, and the like, can also be used.

BEST MODE FOR CARRYING OUT THE INVENTION

The present invention will now be described in more detail with reference to the following Examples that should not be construed as limiting the scope of the invention.

In the following Examples, measurement of the amount of carbon dioxide gas produced during fermentation, and evaluation of a freeze resistance and an invertase activity of yeast strains were conducted in accordance with the following methods.

1. Measurement of the amount of carbon dioxide gas produced during fermentation:

With respect to 30 g of a dough, the amoutn (ml) of carbon dioxide gas produced during fermentation is measured using Fermograph (manufactured by ATTO Co., LTD, Japan), GASOGRAPH (manufactured by D & S Instrument Ltd., U.S.A.) or the like.

2. Freeze resistance:

A fresh dough is prefermented at 30° C. for 60 minutes and subsequently fermented at 38° C. for 60 minutes, and the amount (ml) of carbon dioxide gas produced during the fermentation at 38° C. is measured and taken as the non-freeze fermentative ability.

Separately, the same fresh dough as used above is pre-fermented at 30° C. for 60 minutes and then, frozen at −20° C. for 14 days. After that period of time, the frozen dough is thawed at 38° C. for 20 minutes, and fermented at 38° C. for 60 minutes. The amount (ml) of carbon dioxide gas produced during the fermentation at 38° C. is measured and taken as the post-freeze fermentative ability.

The post-freeze fermentative ability. Freeze resistance is obtained in terms of a post-freeze residual fermentative ability (%), relative to the non-freeze fermentative ability (100%).

3. Measurement of invertase activity:

(1) Preparation of seed yeast:

A loopful of a yeast strain is inoculated into 200 ml of YPD liquid medium (composition of which is shown below) in a 500-ml Erlenmeyer flask and then, cultured at 30° C. for 24 hours while shaking. Then, the resultant culture is inoculated into 15 liters of a molasses culture medium (composition of which is also shown below) in a 30-liter jar fermenter, followed by spinner culturing at 30° C. for 16 hours with aeration, to thereby obtain a seed yeast culture.

| Composition of YPD liquid medium (pH 5.5) | |
|---|---|
| yeast extract (Lot 012701, manufactured by Difco Laboratories, U.S.A.) | 5 g |
| peptone (Lot 018802, manufactured by Difco Laboratories, U.S.A.) | 10 g |
| glucose | 40 g |
| $KH_2PO_4$ | 5 g |
| $MgSO_4 \cdot 7H_2O$ | 2 g |
| distilled water | 1000 ml |

| Composition of molasses culture medium (pH 5.5) | |
|---|---|
| blackstrap molasses (adjusted to 40% sugar, manufactured in Philippines) | 3.5 liters |
| urea | 35 g |
| $NH_4H_2PO_4$ | 30 g |
| $(NH_4)_2 SO_4$ | 30 g |
| distilled water | 11.5 liters |

(2) Main culturing in a 300-liter jar fermenter:

150 Liters of a culture medium for main culturing (composition of which is shown below) is prepared in a 300-liter jar fermenter.

| Composition of culture medium for main culturing | |
|---|---|
| blackstrap molasses* (adjusted to 40% sugar, manufactured in Philippines) | 30 liter |
| urea | 800 g |
| $NH_4H_2PO_4$ | 350 g |
| distilled water | 120 liter |

*The blackstrap molasses is generally fed to the culture medium during the main culturing.

All the seed yeast culture obtained in step (1) above was inoculated into the prepared culture medium and then, main culturing is carried out under the following conditions.

| | |
|---|---|
| Culturing temperature | 30–32° C. |
| Aeration rate | 300–400 liters/minute |
| Spinning rate | 450 rpm |
| pH | 5.0–6–0 |
| Culturing time | 16 hr. |

Immediately after completion of the culturing, the resultant culture is subjected to centrifugation at 1,690 g for 10 minutes to thereby collect cells. The collected cells are subjected to compression-dehydration using a filter cloth, so that the water content and the solids content are adjusted to 67% by weight and 33% by weight, respectively.

(3) Measurement of invertase activity:

200 mg of the compressed yeast obtained in step (2) above is added to 2 ml of 50 mM sucrose solution (0.1M acetic acid-sodium acetate buffer, pH 4.7), and the mixture is incubated at 25° C. for 5 minutes. The resultant reaction mixture is put in boiling water at 100° C. for 1 minute to thereby terminate the reaction, following by cooling. The concentration of glucose produced in the reaction mixture is measured using Biosensor BF-2 (manufactured by KS. SYSTEMS Co., Ltd., Japan) with glucose selective electrodes and a 50 mM phosphate buffer (pH 7.0). The obtained glucose concentration is intrapolated against a calibration curve prepared using a standard invertase (invertase Grade VII from Baker's Yeast, manufactured by SIGMA Chemical Company, U.S.A.), to thereby determine the invertase activity per g of the compressed yeast. When the compressed yeast has a water content which is slightly higher than or lower than 67% (e.g., 60%, 70% or the like), the obtained invertase activity value is corrected so as to comply with that of compressed yeast having a water content of 67% by weight and a solids content of 33% by weight by the following formula:

Invertase activity
(with respect to
compressed yeast
having a solids
content of
33% by weight) = Invertase activity of actually obtained × compressed yeast $$\times \frac{33}{\text{Solids content of actually obtained compressed yeast}}$$

EXAMPLE 1

Production of Diploid Hybrid Strain,
*Saccharomyces cerevisiae* F-26

Step 1: Preculturing

*Saccharomyces cerevisiae* TY-6 strain having a high fermentative ability on a super high sugar content dough and a low invertase activity but having no freeze resistance was provided, and *Saccharomyces cerevisiae* FTD-R strain having a low fermentative ability on a super high sugar content dough but having a high freeze resistance, was also provided. Each of these two strains was individually inoculated on a YPD agar medium plate and percultured at 30° C. for 24 hours.

The mycological properties of each of these two strains mentioned above are as follows:

a. Morphology: circular or elliptic
b. Size: 2 to 10 μm×4 to 15 μm
c. Sporulation: positive
d. Utilization of carbon source:

|  | Assimilation | Fermentation ($CO_2$ production) |
|---|---|---|
| D-glucose | + | + |
| D-galactose | + | + |
| Maltose | + | + |
| Sucrose | + | + |
| Lactose | − | − |
| Galactose | + | + |
| Raffinose | + | ± |
| Starch | − | − | e. Nitrate assimilation: negative
f. Vitamine requirements:

| Biotin | + |
|---|---|
| Folic acid | − |
| Nicotinic acid | − |
| Thiamine | − |
| Riboflavin | − |
| Calcium pantothenate | + |
| Inositol | − |
| Pyridoxine | − |
| p-Aminobenzoic acid | − |

| Composition of YPD agar medium (pH 5.5) | |
|---|---|
| yeast extract (Lot 012701, manufactured by Difco Laboratories, U.S.A.) | 5 g |
| peptone (Lot 018802, manufactured by Difco Laboratories, U.S.A.) | 10 g |
| glucose | 40 g |
| $KH_2PO_4$ | 5 g |

-continued

| Composition of YPD agar medium (pH 5.5) | |
|---|---|
| $MgSO_4 \cdot 7H_2O$ | 2 g |
| agar | 20 g |
| distilled water | 1000 ml |

Step 2: Sporulation

A loopful each of the two precultured strains was individually inoculated and cultured on Sherman's agar medium plate at 25° C. for 6 days to thereby induce sporulation.

| Composition of Sherman's agar medium (pH 7.2) | |
|---|---|
| potassium acetate | 1.0 g |
| yeast extract (Lot 012701, manufactured by Difco Laboratories, U.S.A.) | 0.1 g |
| glucose | 0.05 g |
| agar | 2.0 g |
| distilled water | 100 ml |

Step 3: Isolation of Spores

A loopful each of the two sporulated strains was individually suspended in a solution (2 ml) of a lytic enzyme (trade name "Zymolyase-20T"; β-1,3-glucan lamunaripentaohydrase; 2 to 3 U/ml, manufactured by KIRIN BREWERY Co., Ltd., Japan), and incubated at 30° C. for 30 to 60 minutes. After the above enzyme treatment, spores were isolated from ascus with a micromanipulator.

Step 4: Germination and Production of Haploid Strains

With respect to each of strain TY-6 and strain FTD-R, the isolated spores were placed on the same YPD agar medium plate as mentioned above, and cultured at 30° C. until the spores germinated, thereby producing haploid strains. With respect to each of the produced strains, a test was conducted as to whether or not conjugation occurs between the produced strain and a standard haploid strain (the mating type of which is known) to form a zygote, thereby determining the mating type of the strain.

Step 5: Conjugation

With respect to each of the above-obtained two different classes of haploid strains, i.e., a class of haploid strains obtained from the germination of spores of diploid yeast strain TY-6 having a high fermentative ability on a super high sugar content dough and a low invertase activity but having no freeze resistance and another class of haploid strains obtained from the germination of spores of diploid yeast strain FTD-R having a low fermentative ability on a super high sugar content dough but having a high freeze resistance, each haploid strain was individually (separately according to the class) cultured on the YPD liquid medium (YPD agar medium with its agar removed therefrom) at 30° C. for 4 to 8 hours. A pair of cultures respectively derived from the two different classes of haploid strains were mixed with each other and incubated at 30° C., to thereby form zygotes. The zygotes formed were isolated with a micromanipulator and cultured at 30° C. for 3 days. Thus, a wide variety of types of diploid hybrid strains were obtained.

From the various types of diploid hybrid strains thus obtained, those strains which have a freeze resistance, i.e., a post-freeze residual fermentative ability (in a moderate sugar content dough having a sugar content of 15% by weight, based on the weight of a flour in the dough) of 80% or more, were selected (first screening). The strains selected in the first screening was subjected to a further screening (second screening) to thereby obtain three types of strains having a non-freeze fermentative ability of 45 ml or more in terms of the amount of carbon dioxide gas generated by fermentation at 38° C. for one hour with respect to 30 g of a super high sugar content dough containing 0.935 g of the yeast, wherein the super high sugar content dough has a sugar content of 35% by weight, based on the weight of a flour in the dough. With respect to the three types of strains selected in the second screening, an invertase activity was measured. As a result, it was confirmed that each of the selected strains has an invertase activity in the range of from 50 to 200 U/g, and shows good results in the baking test described below. One of these three types of strains was designated as strain F-26 and deposited with the National Institute of Bioscience and Human-Technology, Japan at the international depositary under the accession number FERM BP-5150 on Jun. 27, 1995. (The strain F-26 was formerly deposited as strain 3-2-C-7 with the National Institute of Bioscience and Human-Technology, Japan at the domestic depositary under the accession number FERM P-14013 on Dec. 10, 1993.)

With respect to the specific types of mating haploid strains produced and used for obtaining strain F-26, the haploid strain obtained from *Saccharomyces cerevisiae* Ty-6 was designated as strain TY-6-1, and the haploid strain obtained from *Saccharomyces cerevisiae* FTD-R was designated as strain FTD-R-1. The invertase activity of the strain TY-6-1 was in the range of from 50 to 200 U/g (compressed yeast), and the invertase activity of the strain FTD-R-1 was in the range of from 500 to 1000 U/g (compressed yeast).

The mycological properties of each of the two strains are as follows:

a. Morphology: circular
b. Size: 2 to 10 μm×2 to 10 μm
c. Sporulation: negative
d. Utilization of carbon source:

|  | Assimilation | Fermentation ($CO_2$ production) |
|---|---|---|
| D-glucose | + | + |
| D-galactose | + | + |
| Maltose | + | + |
| Sucrose | + | + |
| Lactose | − | − |
| Galactose | + | + |
| Raffinose | + | ± |
| Starch | − | − | e. Nitrate assimilation: negative
f. Vitamine requirements:

| Biotin | + |
|---|---|
| Folic acid | − |
| Nicotinic acid | − |
| Thiamine | − |
| Riboflavin | − |
| Calcium pantothenate | + |
| Inositol | − |
| Pyridoxine | − |
| p-Aminobenzoic acid | − |

With respect to the above-obtained diploid hybrid strain F-26, the invertase activity thereof was compared with those of the following commercially available strains. Results are shown in Table 1.

TABLE 1

|  | Invertase activity (U/g) |
|---|---|
| Non-freeze resistant yeast | 1260 |
| Freeze resistant yeast (1) | 1040 |
| Freeze resistant yeast (2) | 18000 |
| Freeze resistant yeast (3) | 860 |
| Freeze resistant yeast (4) | 1510 |
| Freeze resistant yeast (5) | 390 |
| Freeze resistant yeast (6) | 550 |
| Strain F-26 | 140 |

The above results demonstrate that strain F-26 has an invertase activity as low as far less than a half of the invertase activity of any of the commercially available strains examined.

The above comparative strains are also used for comparison with strain F-26 in respect of various performances in the following Examples.

Identification of the above conventional strains of yeast is shown below:

Non-freeze Resistant Yeast:

a commercially available *Saccharomyces cerevisiae* strain 237 NG (trade name: 45 Yeast, manufactured by Asahi Kasei Kogyo Kabushiki Kaisha, Japan)

Freeze Resistant Yeast (1):

a commercially available *Saccharomyces cerevisiae* strain (trade name: F Yeast, manufactured by Asahi Kasei Kogyo Kabushiki Kaisha, Japan)

Freeze Resistant Yeast (2):

a commercially available *Saccharomyces cerevisiae* strain (trade name: FC Yeast, manufactured by Asahi Kasei Kogyo Kabushiki Kaisha, Japan)

Freeze Resistant Yeast (3):

a commercially available *Saccharomyces cerevisiae* strain (trade name: Green Yeast, manufactured by Kaneka Corporation, Japan)

Freeze Resistant Yeast (4):

a commercially available *Torulaspora delbrueckii* strain (trade name: Y yeast, manufactured by Sankyo Co., Ltd., Japan)

Freeze Resistant Yeast (5):

a commercially available *Saccharomyces cerevisiae* strain (trade name: FD-1 yeast, manufactured by Oriental Yeast Co., Ltd., Japan)

Freeze Resistant Yeast (6):

a commercially available *Saccharomyces cerevisiae* strain (trade name: FTS Yeast, manufactured by Kyowa Hakko Kogyo Co., Ltd., Japan)

EXAMPLE 2

Evaluation of Non-freeze Fermentative Ability

In accordance with the recipes indicated in Table 2, ingredients for dough were kneaded for 2 minutes by means of a compact complete mixer (manufactured by National MFG, Co., LTD, U.S.A.), to thereby obtain five types of doughs with different sugar contents (i.e., a non-sugar dough and low to super high sugar content doughs). With respect to each of the doughs, a non-freeze fermentative ability was measured in terms of the amount of carbon dioxide gas generated under fermentation conditions as mentioned above. Results are shown in Table 3.

TABLE 2

|  | Non-sugar dough | Low sugar content dough | Moderate sugar content dough | High sugar content dough | Super high sugar content dough |
|---|---|---|---|---|---|
| Strong flour (trade name: Eagle, manufactured by Nisshin Flour Milling Co., Ltd., Japan) | 20 g | 20 g | 20 g | 20 g | 20 g |
| Sugar | — | 1 g | 3 g | 5 g | 7 g |
| Salt | 0.3 g | 0.3 g | 0.3 g | 0.3 g | 0.3 g |
| Compressed yeast | 1.2 g | 1.2 g | 1.2 g | 1.2 g | 1.2 g |
| Distilled water | 13 ml | 12.4 ml | 12 ml | 11 ml | 10 ml |

TABLE 3

| | Amount of carbon dioxide gas produced (ml) | | | | |
|---|---|---|---|---|---|
| | Non-sugar dough | Low sugar content dough | Moderate sugar content dough | High sugar content dough | Super high sugar content dough |
| Non-freeze resistant yeast | 108 | 182 | 151 | 90 | 40 |
| Freeze resistant yeast (1) | 130 | 174 | 147 | 67 | 31 |
| Freeze resistant yeast (2) | 162 | 181 | 138 | 32 | 11 |
| Strain F-26 | 78 | 165 | 157 | 95 | 52 |

As is apparent from Table 3, strain F-26 of the present invention showed an excellent non-freeze fermentative ability in doughs with medium or higher sugar content, especially in high sugar content and super high sugar content doughs.

EXAMPLE 3

Freeze Resistance (Moderate Sugar Content Dough)

The freeze resistances of moderate sugar content doughs having their respective formulations shown in Example 2 were examined. Results are shown in Table 4. As is apparent from Table 4, strain F-26 of the present invention has a post-freeze residual fermentative ability as high as more than 85%, indicating that it has a very high freeze resistance as compared to the conventional strains of yeasts.

TABLE 4

| | Amount of gas produced (ml) | | Post-freeze residual fermentative ability % |
|---|---|---|---|
| | Non-freeze | Post-freeze | |
| Non-freeze resistant yeast | 167 | 98 | 58.7 |
| Freeze resistant yeast (1) | 164 | 130 | 79.2 |
| Freeze resistant yeast (2) | 157 | 129 | 82.1 |
| F-26 | 171 | 148 | 86.5 |

EXAMPLE 4

Freeze Resistance (High Sugar Content Dough)

The freeze resistances of high sugar content doughs having their respective formulations shown in Example 2 were examined. Results are shown in Table 5. As is apparent from Table 5, strain F-26 of the present invention has a post-freeze residual fermentative ability as high as more than 90%, indicating that it has a very high freeze resistance as compared to the conventional strains of yeasts.

TABLE 5

| | Amount of gas produced (ml) | | Post-freeze residual fermentative ability (%) |
|---|---|---|---|
| | Non-freeze | Post-freeze | |
| Non-freeze resistant yeast | 115 | 72 | 62.6 |
| Freeze resistant yeast (1) | 111 | 97 | 87.4 |
| F-26 | 121 | 113 | 93.4 |

EXAMPLE 5

Baking Test (Production of Bread)

Baking tests were conducted using three types of frozen doughs respectively containing non-freeze resistant yeast, freeze resistant yeast (1) and F-26, each in compressed yeast form.

(1) Sweet bread (dough having a sugar content of 25% by weight, based on the weight of a flour was used)

Baking tests were conducted, under the following conditions, using doughs having a sugar content of 25% by weight, based on the weight of a flour. In these tests, each of the doughs was subjected to panning into a one-loaf shape in order to simplify the comparison in the required time for final proofing. The amount of each portion of dough (in divided form) was 180 g as mentioned below, and the mold size was 12.5 cm×7.5 cm (the depth: 6 cm).

Formulation 1000 g of flour, 30 g of non-fat powdered milk, 60 g of baker's yeast, 100 g of whole egg, 250 g of sugar, 1 g of yeast food, 8 g of salt, 80 g of fat, 5 g of emulsifying agent, and 450 ml of water.

Procedure and Conditions

Operation of mixer (kneading) (in the following order):
    2 minutes at low speed,
    3 minutes at medium speed,
    (addition of fat)
    3 minutes at low speed,
    2 minutes at medium speed, and
    7 to 8 minutes at high speed.

Dough temperature at the time of completion of the kneading (°C.) 20
Fermentation time (min.) 30
Weight of each portion of dough (g) 180
Bench time (min.) 15
Freezing (after molding) at −20° C.
Freezing storage period (days) 28
Thawing temperature (°C.) 20
Thawing time (min.) 150
Proofing temperature (°C.) 38
Proofing time: proofing was conducted until the dough reached the upper edge of the mold (depth: 6 cm).
Baking temperature (°C.) 200
Baking time (min.) 18
Results of the baking tests are shown in Table 6 below.

As is apparent from Table 6, the bread obtained by using strain F-26 of the present invention was a high quality bread having a large volume, an appropriate light brown color, and a lustrous and less mottled surface.

TABLE 6

|  | Non-freeze resistant yeast | Freeze resistant yeast (1) | F-26 |
| --- | --- | --- | --- |
| Proofing time[*1] (min.) | 62 | 52 | 45 |
| Bread volume[*2] (ml) | 810 | 890 | 970 |
| Darkness of color[*3] | 2+ | 2+ | 3+ |
| Surface luster[*4] | 2+ | 2+ | 3+ |
| Mottling (occurrence of fisheyes)[*5] | + | + | 3+ |

(Note)
[*1]: Proofing time: the time required for the dough filled in the mold to reach the upper edge of the mold by expansion due to fermentation.
[*2]: Bread volume: The volume of the bread measured immediately after baking.
[*3]: Criteria for: the evaluation of color: 3+: appropriate, 2+: slightly dark, and +: very dark
[*4]: Criteria for the evaluation of surface luster: 3+: markedly lustrous, 2+: less lustrous, and +: least lustrous
[*5]: Criteria for the evaluation of degree of mottling (occurrence of fisheyes): 3+: low (advantageous) 2+: noticeable, and +: significantly high (2) Sweet bread (dough having a sugar content of 20% by weight, based on the weight of the flour)

Baking tests were conducted, under the following conditions, using doughs having a sugar content of 20% by weight, based on the weight of the flour. For the purpose of examining whether or not a dough was resistant to weakening in mass cohesion during freezing preservation so as to be able to maintain an appropriate firmness and prevent the shape thereof from changing under its own weight even after thawing, the dough was not subjected to panning, but manually shaped into a spherical shape.

Formulation
1000 g of flour, 30 g of non-fat powdered milk, 50 g of baker's yeast, 80 g of whole egg, 200 g of sugar, 1 g of yeast food, 13 g of salt, 80 g of fat, 5 g of an emulsifying agent 5 g, and 480 ml of water.

Procedure and Conditions
Operation of mixer (kneading) (in the following order):
2 minutes at low speed,
3 minutes at medium speed,
(addition of fat)
3 minutes at low speed,
2 minutes at medium speed, and
7 to 8 minutes at high speed.
Dough temperature at the time of completion of the kneading (°C.) 20
Fermentation time (min.) 30
Weight of each portion of dough (g) 50
Bench time (min.) 15
Freezing (after molding) at −20° C.
Freezing storage period (days) 28
Thawing temperature (°C.) 20
Thawing time (min.) 150
Proofing temperature (°C.) 38
Proofing time (min.) 50
Baking temperature (°C.) 200
Baking time (min.) 10
Results of the baking tests are shown in Table 7 below.

As is apparent from Table 7, the bread obtained by using strain F-26 of the present invention was a high quality bread having a large volume, an appropriate light brown color and a less mottled surface. Further, as is also apparent from Table 7, a dough prepared by using strain F-26 of the present invention was resistant to weakening in mass cohesion during the freezing preservation, so that it could maintain an appropriate firmness and prevent the shape thereof from changing under its own weight even after thawing. As a result, the bread had a good shape, as compared to breads produced by using conventional yeasts.

Table 7

|  | Non-freeze resistant yeast | Freeze resistant yeast (1) | F-26 |
| --- | --- | --- | --- |
| Mass cohesion of dough[*1] | + | + | 3+ |
| Bread volume[*2] (ml) | 240 | 264 | 292 |
| Darkness of color[*3] | 2+ | 2+ | 3+ |
| Mottling (occurrence of fisheyes)[*4] | + | + | 3+ |

(Note)
[*1]: Criteria for the evaluation of mass cohesion of dough: 3+: good, 2+: poor, and +: very poor
[*2]: The same criteria as in the footnote of Table 6.
[*3]: The same criteria as in the footnote of Table 6.
[*4]: The same criteria as in the footnote of Table 6.

EXAMPLE 6

Saccharide Composition in the Tissue of the Bread

With respect to each of the breads produced by using freeze-resistant yeast (1) and strain F-26, which breads were used in the baking test (1) in Example 5, the saccharide composition in the tissue of the bread was determined as follows.

5 g of an internal portion of the bread was taken out. 45 g of distilled water was added to the internal portion of the bread, and the resultant mixture was stirred thoroughly and centrifuged to obtain a supernatant. The Saccharide composition of the obtained supernatant was determined by high performance liquid chromatography under the following conditions.

Column: Asahipak NH2P-50 (manufactured by Asahi Kasei Kogyo Kabushiki Kaisha, Japan), I.D.: 4.6 mm, L: 250 mm
mobile phase: $CH_3CN:H_2O=75:25$
Flow rate: 0.8 ml/min.
Detector: RI
Column temperature: 30° C.

The contents and ratios of sucrose, glucose, fructose and maltose in the supernatant are shown in Table 8.

TABLE 8

| | Freeze-resistant yeast (1) | | F-26 | |
|---|---|---|---|---|
| | g of saccharide/100 ml of supernatant | Weight ratio (%) | g of saccharide/100 ml of supernatant | Weight ratio (%) |
| Sucrose | 1.01 | 34.5 | 2.35 | 78.6 |
| Glucose | 0.88 | 30.0 | 0.13 | 4.3 |
| Fructose | 0.80 | 27.3 | 0.25 | 8.4 |
| Maltose | 0.24 | 8.2 | 0.26 | 8.7 |
| Total | 2.93 | 100 | 2.99 | 100 |

As is apparent from Table 8, although there is no significant difference in total content of the above-mentioned saccharides as between the use of freeze-resistant yeast (1) and the use of strain F-26 of the present invention, the ratio of sucrose is remarkably high and the ratios of glucose and fructose are remarkably low in the case of the bread produced using strain F-26, differing from those in the case of the bread produced using freeze-resistant yeast (1). The reason for this is believed to reside in that strain F-26 of the present invention has a low invertase activity and, therefore, the decomposition rate of sucrose in the dough is low, leading to the large amount of sucrose remaining undecomposed. It is known that the maillard reaction between saccharides and amino acids, which is the main cause of the browning of the surface of the bread by baking, is likely to occur when the saccharide is reduced sugar (e.g., fructose and glucose) and unlikely to occur when the saccharide is unreduced sugar (e.g., sucrose). Therefore, it is also believed that the light brown color of the bread produced by using strain F-26 in the baking test (1) in Example 5 is ascribed to the low decomposition rate of sucrose in the dough due to the low invertase activity of strain F-26.

EXAMPLE 7

Baking Tests Using Two Types of Doughs Respectively Containing Sucrose and a Mixture of Glucose and Fructose In order to confirm that the color of the surface of the baked bread depends on the ratio of saccharides in the dough, baking tests were conducted using two types of doughs respectively containing 1) sucrose and 2) a 1:1 mixture of glucose and fructose as follows.

Sweet breads were produced in substantially the same manner as in the baking test (1) of Example 5, except that each of 1) sucrose and 2) a 1:1 mixture of glucose and fructose were individually used as sugar in the dough. The saccharide composition of each of the baked breads was determined according to the method described in Example 6. Results of the baking tests and the saccharide compositions of the respective baked breads are shown in Table 9.

TABLE 9

| | Freeze-resistant yeast (1) | | F-26 | |
|---|---|---|---|---|
| | Sucrose | Glucose+fructose | Sucrose | Glucose+fructose |
| Proofing time (min.) | 52 | 70 | 45 | 54 |
| Bread volume (ml) | 900 | 860 | 970 | 880 |
| Darkness of color | 2+ | + | 3+ | + |
| Surface luster | 2+ | + | 3+ | + |
| Mottling (occurrence of fisheyes) | + | + | 3+ | 2+ |
| Composition of saccharides (wt %) | | | | |
| Sucrose | 33.4 | 0 | 76.7 | |
| Glucose | 29.8 | 40.4 | 5.4 | 42.5 |
| Fructose | 28.5 | 51.2 | 9.2 | 49.0 |
| Maltose | 8.3 | 8.4 | 8.7 | 8.5 |
| Total | 100 | 100 | 100 | 100 |

As is apparent from Table 9, the baked bread obtained by using strain F-26 of the present invention and sucrose as sugar is evaluated as a high quality bread, enjoying the shortest proofing time, the largest bread volume, the lightest color, and a lustrous and least mottled surface. Table 9 also shows that the baked bread obtained by using strain F-26 but using a mixture of glucose and fructose (instead of sucrose) was inferior to the baked bread obtained by using strain F-26 and sucrose in all properties including proofing time, bread volume, color, and degrees of luster and mottling of the surface thereof.

Table 9 also shows that the bread having higher contents of glucose and fructose has a darker color, and the bread having lower contents of glucose and fructose and a lighter color. Therefore, it can be considered that the difference in color between the breads produced in the baking test (1) of Example 5 is caused by the difference in the saccharide composition between the breads.

What is claimed is:

1. A biologically pure culture of the yeast strain *Saccharomyces cerevisiae* F-26, FERM BP-5150.

* * * * *